United States Patent [19]

Howe et al.

[11] 4,284,426
[45] Aug. 18, 1981

[54] 2-CHLORO-4,5-DISUBSTITUTED-THIAZOLES USEFUL AS HERBICIDAL SAFENERS

[75] Inventors: Robert K. Howe, Bridgeton; Len F. Lee, Maryland Heights, both of Mo.

[73] Assignee: Monsanto Company, St. Louis, Mo.

[21] Appl. No.: 80,751

[22] Filed: Oct. 1, 1979

[51] Int. Cl.$^3$ .................... A01N 43/78; C07D 277/20
[52] U.S. Cl. ........................................ 71/90; 47/57.6; 71/118; 548/202; 548/203
[58] Field of Search ................... 548/302, 203; 71/90, 71/118

[56] References Cited

U.S. PATENT DOCUMENTS

| | | | |
|---|---|---|---|
| 2,139,570 | 12/1938 | Andersag et al. | 260/302 |
| 2,186,420 | 1/1940 | Mathes | 260/302 |
| 2,392,935 | 1/1946 | Mathes | 260/302 |
| 2,500,142 | 3/1950 | Wiesehahn | 260/302 |
| 2,776,976 | 1/1957 | D'Amico | 260/302 |
| 3,031,457 | 4/1962 | Charonnat | 260/302 |
| 3,536,727 | 10/1970 | Cavalla et al. | 260/302 |
| 3,833,601 | 9/1974 | Beck et al. | 260/302 R |
| 4,124,372 | 11/1978 | Pallos et al. | 71/118 |
| 4,137,066 | 1/1979 | Gaughan | 71/91 |

FOREIGN PATENT DOCUMENTS 1187620 2/1965 Fed. Rep. of Germany .

OTHER PUBLICATIONS

J. L. Garraway, Pestic. Sci., 1970, vol. 1, pp. 240–243, Growth Regulating Activity of Some Thiazole-and Thiazoline-Acetic Acids.
J. L. Garraway, Pestic. Sci., vol. 5, 1974, pp. 185–188, Growth Regulating Activity of Some Thiazole-and Thiazolidine-Acetic Acids.
G. M. Clarke et al., J. Chem. Soc. (B), 1966, pp. 339–343, Studies in Mass Spectrometry, Part VII, Mass Spectra of Thiazoles.
Derwent Abstract of Great, Britain, patent 1,532,240 published Nov. 1978.
J. Simiti et al., Chem. Abstracts 79:18628b (1973).
Chem. Abstracts, 84: 149270e (1976).

*Primary Examiner*—Donald G. Daus
*Assistant Examiner*—M. C. Eakin
*Attorney, Agent, or Firm*—Patricia A. Coburn; Donald W. Peterson

[57] ABSTRACT 2-chloro-4,5-disubstituted-thiazoles have been found to be effective in reducing herbicidal injury to sorghum plants due to the application thereto of acetanilide and thiocarbamate herbicides.

21 Claims, No Drawings

2-CHLORO-4,5-DISUBSTITUTED-THIAZOLES USEFUL AS HERBICIDAL SAFENERS

This invention relates to novel 2-chloro-4,5-disubstituted-thiazoles as well as their use in compositions and methods for reducing herbicidal injury. More specifically, the invention relates to novel compositions and methods for reducing injury to sorghum plants by herbicides, such as acetanilides and thiocarbamates, which comprises treating the crop plant locus or the seed of the crop plant with an effective amount of a 2-chloro-4,5-disubstituted-thiazoles that will be described more fully below.

BACKGROUND OF THE INVENTION

While acetanilide and thiocarbamate herbicides are very useful for controlling certain weeds, many of the acetanilide and thiocarbamate herbicides also injure crop plants, as for example, sorghum, slowing growth and development of the crop plant at application rates necessary to stunt or kill the weeds. Obviously, a safening agent consisting of a composition that could be used to treat the seed of the crop plant, the crop plant locus or the crop plant itself, resulting in a reduction of injury to the crop plant due to application of the herbicide without a corresponding reduction of herbicidal action on the weed, would be quite beneficial.

DESCRIPTION OF THE INVENTION

In accordance with the novel aspects of the present invention, injury to sorghum plants, due to the application thereto of acetanilide and thiocarbamate herbicides such as 2-chloro-2',6'-diethyl-N-(methoxymethyl)acetanilide (hereinafter referred to by its common name, alachlor), 2-chloro-2',6'-diethyl-N-(butoxymethyl)acetanilide (hereinafter referred to by its common name, butachlor), 2-chloro-N-isopropylacetanilide (hereinafter referred to by its common name, propachlor), S-(2,2,3-trichloroallyl)-diisopropylthiocarbamate (hereinafter referred to by its common name as triallate), S-(2,3-dichloroallyl-diisopropylthiocarbamate (hereinafter referred to by its common name as diallate), may be reduced without a corresponding reduction in injury to the weeds by application to the sorghum locus or the seed of the sorghum plant prior to planting of an effective amount of a safening agent comprising a 2-chloro-4,5-disubstituted-thiazole having the formula:

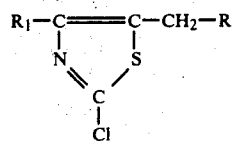

wherein R is equal to halogen, hydroxy, mercapto, methylthio, lower alkyl carbonyloxy, lower alkoxy, lower alkoxy carbonyl, lower alkoxy carbonyl(lower)alkoxy, lower alkoxy thioxomethylthio, benzyloxy,

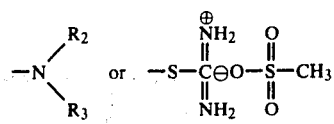

$R_1$ is equal to lower alkyl, halo(lower)alkyl, phenyl or phenyl substituted by one to three groups, which may be the same or different, selected from the group consisting of halogen, lower alkyl, trifluoromethyl and cyano; $R_2$ and $R_3$ independently equal hydrogen, lower alkyl or lower alkenyl.

As used herein, the terms "lower alkyl", "lower alkenyl", "halo(lower)alkyl" and "lower alkoxy" are understood to include alkyl, alkenyl, haloalkyl and alkoxy groups having up to five carbon atoms, inclusive.

The terms "alkyl", "alkenyl" and "alkoxy" are understood to include branched and unbranched groups. When R is alkenyl, allyl is preferred.

The term "halogen" includes bromine, chlorine, fluorine and iodine.

The term "haloalkyl" is understood to mean those alkyl moieties having up to five carbon atoms wherein at least one hydrogen atom has been replaced by halogen atoms. Specifically included are those alkyl moieties in which all of the hydrogen atoms have been replaced by halogen atoms, such as trifluoromethyl or trichloromethyl and the like.

The term "mercapto" refers to the substituent group of having the structure —SH. The term "methylthio" refers to the substituent group having the structure —S—$CH_3$.

The term "lower alkoxy carbonyl" refers to the substituent group whose structure is characterized as

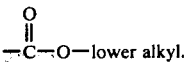

The term "lower alkyl carbonyloxy" refers to the substituent group whose structure is characterized as

The term "lower alkoxy carbonyl(lower)alkoxy" refers to the substituent group whose structure is characterized as

The term "lower alkoxy thioxomethylthio" refers to the substituent group whose structure is characterized as

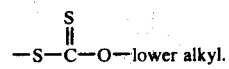

Generally, the 2-chloro-4,5-disubstituted thiazoles of the foregoing formula may be prepared according to the following methods:

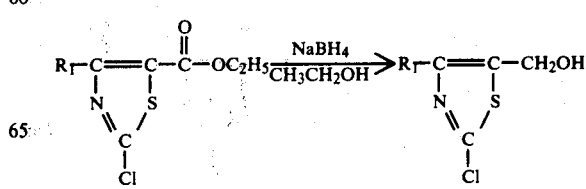

(I)

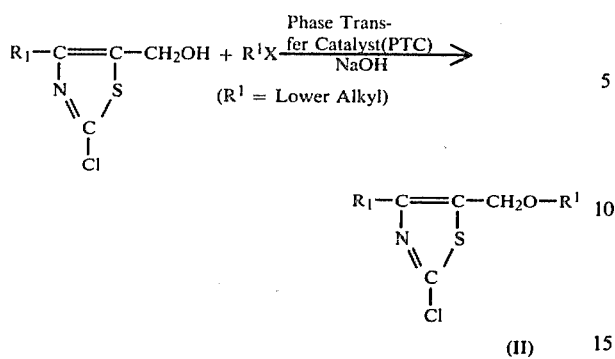
In a similar fashion, the procedure of Method II can be used to prepare the compounds of the invention wherein R is benzoyloxy by substituting a benzyl halide, e.g., benzyl bromide for the alkyl halide used in Method II.
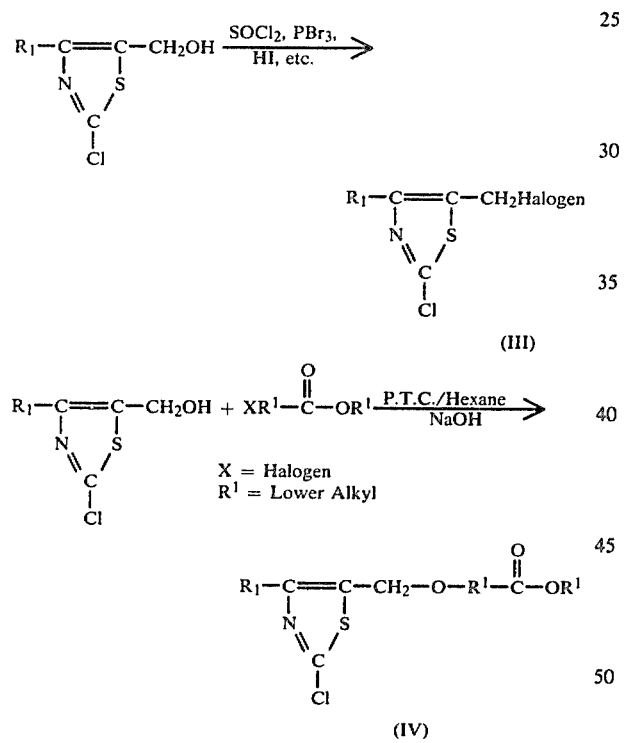
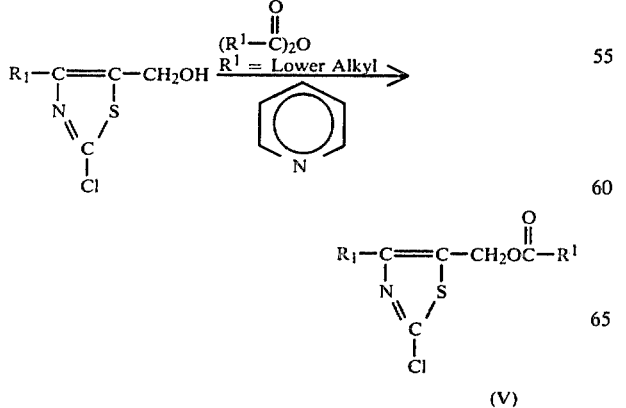
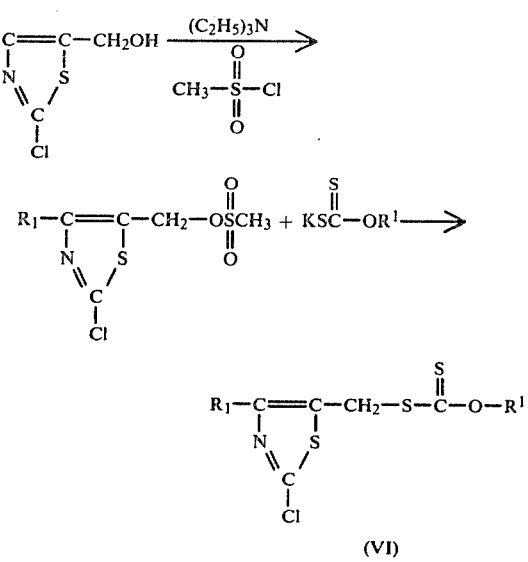
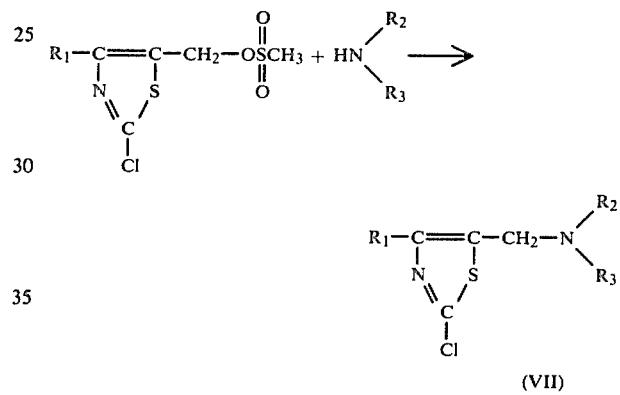
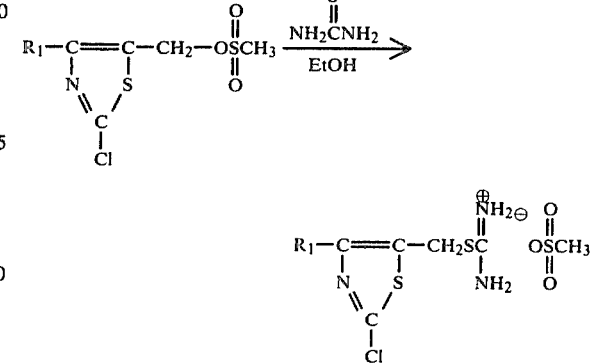
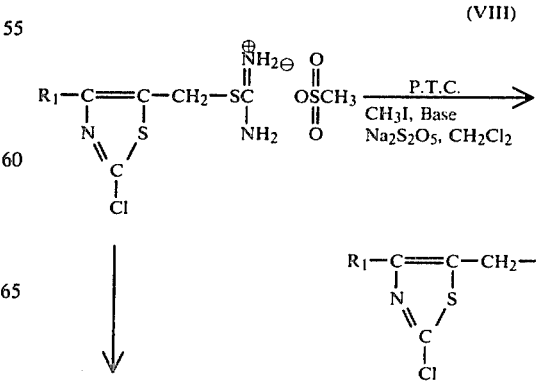

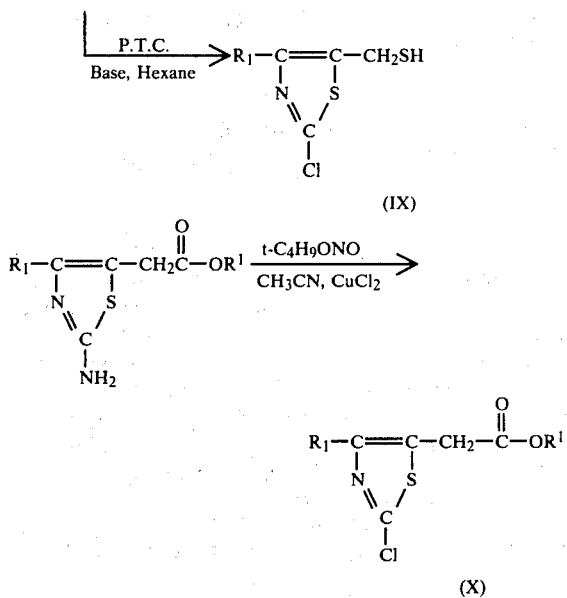

The starting compounds used herein, that is ethyl 2-chloro-4-substituted-5-thiazole carboxylates may be prepared utilizing procedures described in copending applications, Ser. No. 905,682 and Ser. No. 906,183. The 2-amino thiazoles used as the starting material in the procedure of Method X may be prepared by brominating ethyl levulinate followed by reaction of the product with thiourea as described in Beilstein, 13, p. 677 and H. Gregory and L. F. Wiggins, J CHEM SOC, 2, 342 (1947).

In order to more fully illustrate these procedures, the following examples are presented.

EXAMPLE 1

Preparation of Ethyl 2-Chloro-4-Methyl-5-Thiazoleacetate.

To a well stirred mixture of 15.5 g (0.15 mol) of t-butyl nitrite, 16.1 g (0.12 mol) of $CuCl_2$ and 400 ml of acetonitrile, was added 20.07 g (0.1 mol) of ethyl 2-amino-4-methyl-5-thiazole-acetate in 50 min. The reaction mixture was stirred at room temperature for 2 hours and 65° C. for 1 hour. The reaction mixture was filtered and the filtrate was poured into 400 ml of 6 N HCl. The aqueous mixture was extracted with ether and the ether extracts were dried over $MgSO_4$, concentrated to an oil and then Kugelrohr distilled to give 21.7 g of oil. The oil was treated with hexane and filtered. The filtered solid was neutralized with saturated $NaHCO_3$ and filtered. The filtrate was extracted with ether and the ether extract was concentrated to give 1.43 g of oil, which was Kugelrohr distilled at 1.5 mm (pot temperature 115° C.) to give 1.4 g (6.4%) of pure ethyl, 2-chloro-4-(methyl)-5-thiazole-acetate, $n_D25$ 1.5161; bp 123° C. at 8 mm.

The hexane filtrate was treated with saturated $NaHCO_3$ and extracted with ether. The ether extracts were dried over $MgSO_4$ and concentrated. The residual oil, 10.4 g was Kugelrohr distilled to give an additional 5.8 g(21.8%) of ethyl, 2-chloro-4-(methyl)-5-thiazoleacetate, $n_D25$ 1.5143–1.5189.

Anal. Calcd. for $C_8HOCNO_2S$: C, 43.73; H, 4.59; N, 6.38; Cl, 16.14. Found: C, 43.85; H, 4.64; N, 6.39; Cl, 16.12.

EXAMPLE 2

Preparation of 2-Chloro-4-(p-Chlorophenyl)-5-Thiazolemethanol.

To a suspension of 18.2 g (0.06 mol) of ethyl 2-chloro-4-(p-chlorophenyl)-5-thiazolecarboxylate in 100 ml of ethanol was added 2.27 g (0.06 mol) of sodium borohydride. The reaction mixture was stirred for 1 hour and filtered. The ethanol filtrate was concentrated under reduced pressure and the residue was treated with water and extracted with $CHCl_3$. The $CHCl_3$ extracts were dried over $MgSO_4$ and concentrated under reduced pressure. The residual solid (1.5 g) was recrystallized from ethanol-water to give 1.1 g (6%) of 2-chloro-4-(p-chlorophenyl)-5-thiazolemethanol, mp 113°–114° C.

Anal. Calcd. for $C_{10}H_7Cl_2NOS$: C, 46.17; H, 2.71; N, 5.39; Cl, 27.264. Found: C, 46.17; H, 2.73; N, 5.39; Cl, 27.23.

EXAMPLE 3

Preparation of 2-Chloro-4-t-Butyl-5-Thiazolemethanol

To a cold (15° C.) mixture of 24.8 g (0.1 mol) of ethyl 2-chloro-4-t-butyl-5-thiazolecarboxylate and 60 ml of ethanol was added portionwise, 3.79 g (0.1 mol) of sodium borohydride in 20 minutes. The reaction temperature rose spontaneously to 35° C. The reaction mixture was stirred for 2 hours and concentrated to give a residue which was treated with water and extracted with ether. The ether extracts were dried over $MgSO_4$ and concentrated under reduced pressure to give 22.9 g of oil. The oil was chromatographed on silica gel using ether-petroleum ether (5:95, v/v) as eluant. The first fraction gave 13.0 g of the starting thiazolecarboxylate; the second fraction gave 0.3 g of impure ethyl 4-t-butyl-5-thiazolecarboxylate. The third fraction gave 6.6 g of an oil which was Kugelrohr distilled at 0.7 mm (pot temperature 102° C.) to give 6.4 g (31%) of 2-chloro-4-t-butyl-5-thiazolemethanol, $n_D25$ 1.5436.

Anal. Calcd. for $C_8H_{12}ClNOS$: C, 46.70; H, 5.88; N, 6.81; Cl, 17.24. Found: C, 46.68; H, 5.89; N, 6.81; Cl, 17.23.

EXAMPLE 4

Preparation of 2-Chloro-4-Trifluoromethyl-5-Thiazolemethanol

To a mixture of 2.6 g (0.01 mol) of ethyl 2-chloro-4-(trifluoromethyl)-5-thiazolecarboxylate and 10 ml of ethanol was added. 0.62 g of sodium cyanoborohydride. The reaction mixture was stirred for 5 minutes and 0.40 g of sodium borohydride was added. The temperature of the reaction mixture raised spontaneously to boiling point. The reaction mixture was stirred for 30 minutes and quenched with water. The aqueous mixture was extracted with ether. The ether solution was dried over $CaSO_4$ and concentrated under reduced pressure. The residue was crystallized from petroleum ether to give 1.6 g (74%) of 2-chloro-4-(trifluoromethyl)-5-thiazolemethanol, mp 39°–45° C.

Anal. Calcd. for $C_5H_3ClF_3NOS$: C, 27.60; H, 1.39; N, 6.44; Cl, 16.29. Found: C, 27.61; H, 1.41; N, 6.44; Cl, 16.25.

EXAMPLE 5

Preparation of 2-Chloro-4-(p-Fluorophenyl)-5-Thiazolemethanol

To 1.7 g (0.006 mol) of ethyl 2-chloro-4-(p-fluorophenyl)-5-thiazolecarboxylate in 20 ml of DMF was added 0.22 g (0.006 mol) of sodium borohydride. The reaction temperature raised spontaneously to 28° C. in 30 minutes. To the reaction mixture was added an additional 0.22 g (0.006 mol) of sodium borohydride. The reaction mixture was stirred for 30 minutes and quenched with water. The aqueous mixture was extracted with ether and the ether solution was washed twice with water, dried over $MgSO_4$ and concentrated under reduced pressure to give 1.4 g of oil which was chromatographed on silica gel. The first fraction (500 ml of 5% ethyl acetate-petroleum ether as eluant) was 0.1 g of recovered starting thiazolecarboxylate, mp. 111°–112° C. The second fraction (300 ml of 10% ethyl acetate-petroleum ether as eluant) gave 0.65 g of a waxy material. The third fraction (200 ml of 15% ethyl acetate-petroleum ether as eluant) was 0.2 g (16%) of white solid which was recrystallized from petroleum ether to give 0.16 g of 2-chloro-4-(p-fluorophenyl)-5-thiazolemethanol, mp 97°–98.5° C.

Anal. Calcd. for $C_{10}H_7ClF\ NOS$: C, 49.28; H, 2.90; N, 5.75, Cl, 14.55. Found: C, 49.24; H, 2.90; N, 5.74; Cl, 14.53.

EXAMPLE 6

Preparation of 2-Chloro-5-(Chloromethyl)-4-(Trifluoromethyl)-Thiazole

To 6.73 g (0.031 mol) of the compound of Example 4 was added 15 ml of thionyl chloride. The reaction mixture was heated on a steam bath for 5 minutes. Excess thionyl chloride was removed under reduced pressure and the residue was Kugelrohr distilled at 8 mm to give 6.9 g of yellow oil (pot temperature 100°–105° C.), $n_D{}^{25} = 1.4816$. This material was further distilled on a short path still, to give 6.1 g of yellow oil, $n_D{}^{25} = 1.4856$. This material was purified by column chromatography on silica gel. The first 1 l eluate (5% ether-petroleum ether) gave 5.9 g of oil which was distilled at 6 mm to give 5.28 g (72%) of 2-chloro-5-(chloromethyl)-4-(trifluoromethyl)thiazole as a colorless liquid, bp 80°–82° C., $n_D{}^{25} = 1.4886$.

Anal. Calcd. for $C_5H_2Cl_2F_3NS$: C, 25.44; H, 0.86; N, 5.93. Found: C, 25.50; H, 0.89; N, 5.93.

EXAMPLE 7

Preparation of [2-Chloro-4-(Trifluoromethyl)-5-Thiazole]Methyl Acetate

To a solution of 6.53 g (0.03 mol) of 2-chloro-4-(trifluoromethyl)-5-thiazolemethanol and 3.5 g (0.034 mol) of acetic anhydride in 20 ml of ether was added 2.7 g (0.034 mol) of pyridine. The reaction mixture was stirred for 1 hour. To the reaction mixture was added additional 3.02 g of acetic anhydride and the mixture was stirred for 2 hours. The ether solution was washed successively with water, sodium bicarbonate, and diluted hydrochloric acid, then was dried over $CaSO_4$ and concentrated under reduced pressure. The residue was Kugelrohr distilled to give 6.2 g (86%) of [2-chloro-4-(trifluoromethyl)-5-thiazole]methyl acetate as colorless liquid, $n_D{}^{25} = 1.4631$.

Anal. Calcd. For $C_7H_5ClF_3NO_2S$: C, 32.38; H, 1.97; N, 5.40. Found: C, 32.48; H, 1.97; N, 5.42.

EXAMPLE 8

Preparation of 2-Chloro-4-(Trifluoromethyl)-5-[(Benzyloxy)Methyl]-Thiazole

A mixture of 4.34 g (0.02 mol) of the compound of Example 4, 14.1 g (0.0825 mol) of benzyl bromide, 0.1 g of Aliquat 336 (tradename of phase transfer catalyst available from the General Mills Co.) 25 ml of hexane, 15 ml of 50% sodium hydroxide, and 15 ml of water was held at reflux for 30 minutes. The hexane layer was separated, dried over $MgSO_4$ and concentrated under reduced pressure. The residue (6.8 g) was Kugelrohr distilled at 2 mm (pot temperature 120°–130° C.) to give 5.0 g (81% yield) of 2-chloro-4-(trifluoromethyl)-5-[(benzyloxy)-methyl]-thiazole $n_D{}^{25}$ 1.5215.

Anal. Calcd. for $C_{12}H_9ClF_3NOS$: C, 46.83; H, 2.95; N, 4.55. Found: C, 46.88; H, 2.97; N, 4.56.

EXAMPLE 9

Preparation of 2-Chloro-4-(Trifluoromethyl)-5-(Methoxymethyl)-Thiazole

To a well stirred mixture of 2.16 g (0.01 mol) of the compound of Example 4, 21.5 g of methyl iodide, 0.1 g of Aliquat 336 (tradename for phase transfer reagent available from General Mills Co.) and 25 ml of hexane was added 13 ml of 50% sodium hydroxide. A precipitate formed immediately. To the above mixture was added 13 ml of water whereupon part of the precipitate gradually dissolved. The reaction mixture was held at reflux for 1 hour. An additional 2.16 g (0.01 mol) of the compound of Example 4 and 17.3 g of methyl iodide were added to the reaction mixture and the mixture was held at reflux for 3 additional hours. The hexane layer was separated, dried over $MgSO_4$ and concentrated to give a residue (5.4 g) which was Kugelrohr distilled at 2 mm (pot temperature 80° C.) to give 4.16 g (68% yield) of 2-chloro-4-(trifluoromethyl)-5-(methoxymethyl)-thiazole, $n_D{}^{25}$ 1.4694.

Anal. Calc. For $C_6H_5ClF_3NOS$: C, 30.98; H, 2.27; N, 6.02. Found: C, 31.11; H, 2.18; N, 6.05.

EXAMPLE 10

Preparation of t-Butyl {[2-Chloro-4-(Trifluoromethyl)-5-Thiazolyl]Methoxy} Acetate A mixture of 4.32 G (0.02 Mol) of the compound of Example 4, 0.1 g of Aliquat 336, 3.9 g of t-butyl bromoacetate, 50 ml of hexane, 10 g of sodium hydroxide and 24 ml of water was held at reflux for 1 hour. The reaction mixture was filtered. The hexane layer was separated, dried over $MgSO_4$ and concentrated under reduced pressure. The residue (1.6 g) was chromatographed on silica gel using ether-petroleum ether (2:98 v/v) as eluant. The first fraction gave 1.1 g (16.5%) of t-butyl {[2-chloro-4-(trifluoromethyl)-5-thiazolyl]methoxy} acetate, as an oil, $n_D{}^{25}$ 1.4607.

Anal. Calcd. for $C_{11}H_{13}ClF_3NO_3S$: C, 39.82; H, 3.95; N, 4.22; Cl, 10.69. Found: C, 39.91; H, 4.00; N, 4.20; Cl, 10.65.

EXAMPLE 11

Preparation of
S-{[Chloro-4-(Trifluoromethyl)-S-Thiazolyl]Methyl}-O-Ethyl Carbonodithioate To a cold (0° C.) solution of 34.7 g (0.161 mol) of the compound of Example 4 in 150 ml of toluene there was added over a 30 minute period, 18.2 g (0.18 mol) of triethylamine. To this mixture was added 20.5 g (0.18 mol) of methanesulfonyl chloride. The reaction mixture was stirred at room temperature for 2 hours and was allowed to stand in the refrigerator for 4 days. The insoluble salt was filtered and the filtrate was concentrated under reduced pressure. The residue was dissolved in ether and the ether solution was washed with water, dried over $MgSO_4$ and concentrated under reduced pressure to give 43.8 g (92%) of crude [2-chloro-4-(trifluoromethyl)thiazol-5-yl]methyl methanesulfonate. A 5.5 g portion of the crude material was dissolved in 50 ml of acetone. To this solution was added 2 g (0.0169 mol) of potassium xanthogenate. The reaction mixture was stirred for 2 hours at room temperature and filtered. The acetone filtrate was concentrated to give 6.9 g of oil which was chromatographed on silica gel using ether petroleum ether (1:9 v/v) as eluant. The earlier fraction was 4.1 g (69.9%) of S-[2-chloro-4-(trifluoromethyl)-5-thiazolyl]methyl O-ethyl carbonodithioate; $n_D^{25}$ 1.5497–1.5517.

Anal. Calcd. for $C_8H_7ClF_3NOS_3$: C, 29.86; H, 2.19; N, 4.35; S, 29.89. Found: C, 29.86; H, 2.19; N, 4.34; S, 29.94.

EXAMPLE 12

Preparation of N,N-Dibutyl [2-Chloro-4-(Trifluoromethyl)-5-Thiazole]Methanine

To a cold (−65° C.) solution of 6.0 g (0.02 mol) of [2-chloro-4-(trifluoromethyl)thiazol-5-yl]methyl methanesulfonate (prepared by procedure described in Example 11) in 20 ml of anhydrous ether was added dropwise a solution of 2.57 g (0.02 mol) of dibutylamine in 10 ml of ether in 10 minutes. The reaction mixture was allowed to warm to room temperature and was stirred at room temperature for 18 hours. The ether solution was washed with saturated $NaHCO_3$, dried over $MgSO_4$ and concentrated under reduced pressure. The residue (6.3 g) contained 45% of unreacted starting material. This material was chromatographed on silica gel using ethyl acetate-petroleum ether (3:97 v/v) as eluant. The first fraction was 2.7 g of N,N-dibutyl[2-chloro-4-(trifluoromethyl)-5-thiazole]methanine. $n_D^{25}$ 1.4687.

Anal. Calcd. for $C_{13}H_{20}ClF_3N_2S$: C, 47.48; H, 6.13; N, 8.52. Found: C, 47.58; H, 6.15; N, 8.48.

EXAMPLE 13

Preparation of
S{[2-Chloro-4-(Trifluoromethyl)-5-Thiazolyl]Methyl}-Carbaminidothioate Methanesulfonic Acid Salt A mixture of 6.0 g (0.02 mol) of 2-chloro-4-(trifluoromethyl)thiazol-5-yl-methyl methane sulfonate (prepared by procedure described in Example 11), 1.36 g (0.018 mol) of thiourea and 50 ml of ethanol was held at 75° C. for 10 minutes. The ethanol was removed under reduced pressure and the residue was triturated with ether. The insoluble white powders were separated to give 6.6 g of S{[2-chloro-4-(trifluoromethyl)-5-thiazolyl]methyl}carbaminidothioate methanesulfonic acid salt. mp 164°–168° C.

Anal. Calcd. for $C_7H_9ClF_3N_3O_3S_3$: C, 22.61; H, 2.44; N, 11.30. Found: C, 22.73; N, 2.44; N, 11.30.

EXAMPLE 14

Preparation of
2-Chloro-5-[(Methylthio)methyl]-4-(Trifluoromethyl)-Thiazole

A mixture of 3.72 g (0.01 mol) of the compound of Example 13, 2 g of calcium carbonate, 1 g of sodium metabisulfite, 0.1 g of benzyltriethylammonium chloride, 5.2 g (0.03 mol) of methyl iodide, 50 ml of water and 25 ml of methylene chloride was stirred for 13 hours and filtered. The methylene chloride solution was dried over $MgSO_4$ and concentrated to give 2.4 g of an oil which was Kugelrohr distilled at 2 mm to give 2.1 g of an oil. The material was chromatographed on silica gel using ethyl acetate petroleum ether (3:97 v/v) as eluant. The first fraction (Rf=0.65) was 1.8 g of oil which was Kugelrohr distilled to give 1.77 g (71%) of 2-chloro-5-[(methylthio)methyl]-4-(trifluoromethyl) thiazole as a colorless oil, $n_D^{25}$ 1.5115.

Anal. Calcd. for $C_6H_5ClF_3NS_2$: C, 29.09; H, 2.03; N, 5.66. Found: C, 28.85; H, 1.69; N, 5.61.

EXAMPLE 15

Preparation of
2-Chloro-4-(Trifluoromethyl)-5-Thiazole Methanethiol

A mixture of 7.42 g (0.02 mol) of the compound of Example 13, 2.4 g (0.06 mol) of sodium hydroxide, 0.1 g of benzyltriethylammonium chloride, 24 ml of hexane and 24 ml of hexane and 24 ml of water was stirred under nitrogen for 3.5 hours and filtered. The reaction mixture was extracted with ether. The ether layer was dried over $MgSO_4$ and concentrated under reduced pressure to give 0.6 g of 2-chloro-4-(trifluoromethyl)-5-thiazole methanethiol, $n_D^{25}$ 1.5173. The aqueous layer was neutralized with conc. HCl and extracted with ether. The ether layer was dried over $MgSO_4$ and concentrated under reduced pressure to give 2.1 g of an oil. The oil was Kugelrohr distilled at 2 mm to give two fractions. The second fraction gave 0.9 g of 2-chloro-4-(trifluoromethyl)-5-thiazole methanethiol. The first fraction (0.7 g) was chromatographed on a silica gel plate using ethyl acetate-petroleum ether (1:9 v/v) as eluant. The separated material was Kugelrohr distilled to give 0.45 g of 2-chloro-4-(trifluoromethyl)-5-thiazole methanethiol, $n_D^{25}$ 1.5169.

Anal. Calcd. for $C_5H_3ClF_3NOS_2$: C, 25.70; H, 1.29; N, 6.01. Found: C, 25.68; H, 1.32; N, 5.95.

EXAMPLE 16

Preparation of
2-Chloro-4-Isopropyl-5-Thiazolemethanol

To a mixture of 8.0 g (0.034 mol) of ethyl, 2-chloro-4-isopropyl-5-thiazolecarboxylate and 20 ml of ethanol was added 1.3 g (0.034 mol) of sodium borohydride in 10 minutes. The reaction mixture was stirred at room temperature for 30 minutes and concentrated under reduced pressure. The residue was chromatographed on 250 g of silica gel using ether petroleum ether (1:9, v/v) as eluant. The first fraction (2.2 g) was recovered starting material. The second fraction (3.4 g) was Kugelrohr distilled at 0.5 mm (pot temperature 95° C.)

go give 2.7 g (40%) of 2-chloro-4-isopropyl-5-thiazolemethanol as a colorless liquid, $n_D^{25}$ 1.5425.

Anal. Calcd. for $C_7H_{10}ClNOS$: C, 43.86; H, 5.63; N, 7.31. Cl, 18.50. Found: C, 43.86; H, 5.60; N, 7.28; Cl, 18.48.

In accordance with the novel aspects of the present invention, the 2-chloro-4-substituted-5-substituted-thiazoles are useful for reducing herbicidal injury to sorghum plants. The amount of safening agent employed in the method and compositions of the invention will vary depending upon the manner of application, rate of application, environmental factors as well as other factors known in the art. In each instance, the amount employed is a safening effective amount, i.e., the amount which reduces crop injury by the herbicide.

The amount of herbicide employed is well within the skill of the art and is disclosed in various patents. Propachlor and its herbicidal use is disclosed in U.S. Pat. No. 2,863,752 and Reissue 26,961. Alachlor and butachlor and their herbicidal use are disclosed in U.S. Pat. Nos. 3,442,945 and 3,547,620. U.S. Pat. No. 3,330,821 discloses and claims triallate and diallate herbicides; their herbicidal use is described in U.S. Pat. No. 3,330,643.

The safening agent may be applied to the plant locus in a mixture with the herbicide or it may be applied directly to the sorghum seed itself. By application to the "plant locus" is meant application to the plant growing medium, such as the soil, as well as the seeds, emerging seedlings, roots, stems, leaves, flowers, fruits or other plant parts.

To illustrate the effectiveness of the 2-chloro-4,5-disubstituted-thiazoles, the following examples are presented. These examples are presented merely as being illustrative of the novel aspects of the invention and are not intended to be a limitation as to the scope thereof.

EXAMPLE 17

A good grade of top soil is placed in a container and compacted to a depth of approximately 1.27 cm. from the top of said container. A predetermined number of sorghum seeds are placed on top of the soil. A quantity of soil sufficient to substantially fill the container is measured and placed in a second container. A measured quantity of the safening agent dispersed or dissolved in a suitable carrier is applied to the soil in the second container. A measured quantity of the herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and acetamide herbicide and the pots are leveled. The pots are then placed on a sand bench in the greenhouse and watered from below as needed. The plants are observed at the end of approximately 21 days and the results in terms of percent inhibition of each seed lot are recorded. For each test series, a pot is also prepared containing no herbicide and no safening agent as a control. For each series of tests, the herbicidal effect of the herbicide is observed from pots treated with the same quantity of herbicide alone. The "safening effect" is determined by adding the herbicidal effect of the herbicide when applied alone to the herbicidal effect of the safening agent when applied alone (in no instance, however, will this sum be greater than 100) and subtracting from that the herbicidal effect obtained when both the herbicide and safening agent are incorporated into the soil as discussed above.

Table I summarizes the results obtained when the compounds of the invention were tested in accordance with the procedure of Example 17 utilizing triallate as the herbicide and sorghum as the crop plant.

TABLE I

| Safening Agent Compound of Example No. | Rate of Safening Agent (kg/h) | Rate of Triallate Herbicide (kg/h) | Safening Effect |
| --- | --- | --- | --- |
| 1 | 17.92 | 0.56 | 45 |
| 2 | 8.96 | 0.56 | * |
| 3 | 8.96 | 0.56 | 60 |
| 4 | 17.92 | 0.56 | 60 |
| 5 | 8.96 | 0.56 | * |
| 6 | 8.96 | 0.56 | 80 |
| 7 | 8.96 | 0.56 | 40 |
| 8 | 8.96 | 0.56 | 30 |
| 9 | 8.96 | 0.56 | 20 |
| 10 | 8.96 | 0.56 | 66 |
| 11 | 8.96 | 0.56 | 46 |
| 12 | 8.96 | 0.56 | 50 |
| 13 | 8.96 | 0.56 | 40 |
| 14 | 8.96 | 0.56 | 50 |
| 15 | 8.96 | 0.56 | 50 |
| 16 | 8.96 | 0.56 | 50 |

*Safening effect was between 0 and 19

Table II summarizes the results obtained when the compounds of the invention were tested in accordance with the procedure of Example 17 utilizing alachlor as the herbicide and sorghum as the crop plant.

TABLE II

| Safening Agent Compound of Example No. | Rate of Safening Agent (kg/h) | Rate of Alachlor Herbicide (kg/h) | Safening Effect |
| --- | --- | --- | --- |
| 1 | 17.92 | 2.24 | 20 |
| 2 | 8.96 | 2.24 | * |
| 3 | 8.96 | 2.24 | 50 |
| 4 | 17.92 | 2.24 | 40 |
| 5 | 8.96 | 4.48 | 20 |
| 6 | 8.96 | 2.24 | 28 |
| 7 | 8.96 | 2.24 | 53 |
| 8 | 8.96 | 2.24 | 52 |
| 9 | 8.96 | 2.24 | 52 |
| 10 | 8.96 | 2.24 | 49 |
| 11 | 8.96 | 2.24 | 44 |
| 12 | 8.96 | 2.24 | 20 |
| 13 | 8.96 | 2.24 | 40 |
| 14 | 8.96 | 2.24 | 20 |
| 15 | 8.96 | 2.24 | 40 |
| 16 | 8.96 | 2.24 | 50 |

*Safening effect was between 0 and 19

Table III summarizes the results obtained when the compounds of the invention were tested in accordance with the procedure of Example 17 utilizing butachlor as the herbicide and sorghum as the crop plant.

TABLE III

| Safening Agent Compound of Example No. | Rate of Safening Agent (kg/h) | Rate of Butachlor Herbicide (kg/h) | Safening Effect |
| --- | --- | --- | --- |
| 1 | 17.92 | 6.72 | 20 |
| 2 | 8.96 | 6.72 | * |
| 3 | 8.96 | 6.72 | 50 |
| 4 | 17.92 | 6.72 | 25 |
| 5 | 8.96 | 6.72 | * |
| 6 | 8.96 | 6.72 | 35 |
| 7 | 8.96 | 6.72 | 40 |

TABLE III-continued

| Safening Agent Compound of Example No. | Rate of Safening Agent (kg/h) | Rate of Butachlor Herbicide (kg/h) | Safening Effect |
|---|---|---|---|
| 8 | 8.96 | 6.72 | 25 |
| 9 | 8.96 | 6.72 | 25 |
| 10 | 8.96 | 6.72 | 35 |
| 11 | 8.96 | 6.72 | 35 |
| 12 | 8.96 | 6.72 | 20 |
| 13 | 8.96 | 6.72 | 30 |
| 14 | 8.96 | 6.72 | 30 |
| 15 | 8.96 | 6.72 | 20 |
| 16 | 8.96 | 6.72 | 20 |

*Safening effect was between 0 and 19

As noted previously, the 2-chloro-4,5-disubstituted thiazoles of the present invention can be used to protect crops from the herbicidal activity of the thiocarbamate or acetanilide herbicide without a corresponding diminution in herbicidal activity to the weeds. Examples 18 and 19 illustrate such activity.

EXAMPLE 18

A good grade of top soil is placed in a plastic pot and compacted to a depth of approximately 1.27 cm. from the top of said pot. A predetermined number of crop seeds and weed seeds are placed on top of the soil. A cover layer, approximately 1.27 cm., is placed on top of said seeds. The soil is then treated with a mixture of the safening agent and alachlor dispersed or dissolved in a suitable solvent. For each test series, pots are treated with only the herbicide. Additionally, pots are treated with only the safening agent. The herbicidal effect is observed approximately 21 days after treatment.

Table IV summarizes the results obtained when several of the compounds of the invention were tested in accordance with the procedure of Example 18.

TABLE IV

| Safening Agent Compound of Example No. | Rate of Alachlor Herbicide (lb/acre) - Rate Same For (A) and (B) | Rate of Safening Agent (lb/acre) (A) | Rate of Safening Agent (lb/acre) (B) | (A) (Inhibition Due to Effects of Herbicide) Sorghum | (A) (Inhibition Due to Effects of Herbicide) Green Foxtail | (B) (Inhibition Due to Effects of Herbicide plus safening agent) Sorghum | (B) (Inhibition Due to Effects of Herbicide plus safening agent) Green Foxtail |
|---|---|---|---|---|---|---|---|
| 3 | 0.5 | 0 | 8.0 | 70 | 98 | 0— | 98 |
|   | 1.0 | 0 | 8.0 | 85 | 100 | 0— | 99 |
|   | 2.0 | 0 | 8.0 | 92 | 100 | 30— | 100 |
|   | 4.0 | 0 | 8.0 | 95 | 100 | 50— | 100 |
| 5 | 0.5 | 0 | 8.0 | 35 | — | 90 | — |
|   | 1.0 | 0 | 8.0 | 80 | — | 90 | — |
|   | 2.0 | 0 | 8.0 | 95 | — | 95 | — |
|   | 4.0 | 0 | 8.0 | 98 | — | 100 | — |
| 6 | 0.5 | 0 | 8.0 | 70 | 80 | 0— | 80 |
|   | 1.0 | 0 | 8.0 | 75 | 98 | 10— | 98 |
|   | 2.0 | 0 | 8.0 | 88 | 98 | 20— | 99 |
|   | 4.0 | 0 | 8.0 | 90 | 99 | 25— | 100 |
| 7 | 0.5 | 0 | 8.0 | 70 | 80 | 0— | 85 |
|   | 1.0 | 0 | 8.0 | 75 | 98 | 0— | 98 |
|   | 2.0 | 0 | 8.0 | 88 | 98 | 20— | 98 |
|   | 4.0 | 0 | 8.0 | 90 | 99 | 20— | 99 |
| 6 | 0.5 | 0 | 8.0 | 8 | 90 | 0— | 95 |
|   | 1.0 | 0 | 8.0 | 40 | 90 | 10— | 98 |
|   | 2.0 | 0 | 8.0 | 53 | 97 | 0— | 100 |
|   | 4.0 | 0 | 8.0 | 55 | 99 | 55 | 100 |
| 7 | 0.5 | 0 | 8.0 | 8 | 90 | 0 | 95 |
|   | 1.0 | 0 | 8.0 | 40 | 90 | 0— | 98 |
|   | 2.0 | 0 | 8.0 | 53 | 97 | 0— | 100 |
|   | 4.0 | 0 | 8.0 | 55 | 99 | 0— | 100 |
| 8 | 0.5 | 0 | 8.0 | 80 | 90 | 10— | 99 |
|   | 1.0 | 0 | 8.0 | 90 | 98 | 20— | 100 |
|   | 2.0 | 0 | 8.0 | 95 | 99 | 30— | 98 |
|   | 4.0 | 0 | 8.0 | 98 | 100 | 40— | 100 |
| 9 | 0.5 | 0 | 8.0 | 80 | 90 | 0— | 98 |
|   | 1.0 | 0 | 8.0 | 90 | 98 | 0— | 98 |
|   | 2.0 | 0 | 8.0 | 95 | 99 | 20— | 100 |
|   | 4.0 | 0 | 8.0 | 98 | 100 | 80 | 100 |
| 10 | 0.5 | 0 | 8.0 | 60 | 99 | 10— | 100 |
|   | 1.0 | 0 | 8.0 | 80 | 99 | 50— | 100 |
|   | 2.0 | 0 | 8.0 | 90 | 100 | 60— | 100 |
|   | 4.0 | 0 | 8.0 | 95 | 100 | 40— | 100 |
| 11 | 0.5 | 0 | 8.0 | 60 | 99 | 45 | 100 |
|   | 1.0 | 0 | 8.0 | 80 | 99 | 50— | 100 |
|   | 2.0 | 0 | 8.0 | 90 | 100 | 60— | 100 |
|   | 4.0 | 0 | 8.0 | 95 | 100 | 75— | 100 |
| 12 | 0.5 | 0 | 8.0 | 80 | 98 | 30— | 99 |
|   | 1.0 | 0 | 8.0 | 85 | 98 | 50— | 100 |
|   | 2.0 | 0 | 8.0 | 90 | 99 | 50— | 100 |
|   | 4.0 | 0 | 8.0 | 100 | 100 | 100 | 100 |
| 13 | 0.5 | 0 | 8.0 | 80 | 98 | 0— | 99 |
|   | 1.0 | 0 | 8.0 | 85 | 98 | 10— | 100 |
|   | 2.0 | 0 | 8.0 | 90 | 99 | 20— | 100 |
|   | 4.0 | 0 | 8.0 | 100 | 100 | 45 | 100 |
| 14 | 0.5 | 0 | 8.0 | 80 | 98 | 10— | 98 |
|   | 1.0 | 0 | 8.0 | 85 | 98 | 20— | 100 |
|   | 2.0 | 0 | 8.0 | 90 | 99 | 50— | 100 |
|   | 4.0 | 0 | 8.0 | 100 | 100 | 80— | 100 |

TABLE IV-continued

| Safening Agent Compound of Example No. | Rate of Alachlor Herbicide (lb/acre) - Rate Same For (A) and (B) | Rate of Safening Agent (lb/acre) | | % Inhibition | | | |
|---|---|---|---|---|---|---|---|
| | | | | (A) (Inhibition Due to Effects of Herbicide) | | (B) (Inhibition Due to Effects of Herbicide plus safening agent) | |
| | | (A) | (B) | Sorghum | Green Foxtail | Sorghum | Green Foxtail |
| 15 | 0.5 | 0 | 8.0 | 50 | 98 | 0 — | 95 |
| | 1.0 | 0 | 8.0 | 70 | 99 | 10 — | 98 |
| | 2.0 | 0 | 8.0 | 95 | 99 | 20 — | 98 |
| | 4.0 | 0 | 8.0 | 98 | 99 | 80 | 100 |
| 16 | 0.5 | 0 | 8.0 | 70 | 98 | 0 — | 100 |
| | 1.0 | 0 | 8.0 | 80 | 99 | 30 — | 100 |
| | 2.0 | 0 | 8.0 | 90 | 100 | 30 — | 100 |
| | 4.0 | 0 | 8.0 | 100 | 100 | 40 — | 100 |

— Denotes Significant Safening Effect.

The compounds of the present invention may be applied to sorghum seed as a seed treatment, prior to planting. Seed treatment with the safening agents of the present invention as opposed to soil incorporation or spray application of the safening agent, requires smaller amounts of safening agent and is thus oftentimes a desirable alternative to the above-mentioned modes of applying the safening agents described herein. Example 19 illustrates the use, as seed treatment agents, of certain of the safening agents of the present invention.

EXAMPLE 19

Sorghum seed was treated with safening agent dissolved in methylene chloride. Both untreated and treated sorghum seed were planted in 9½×5¼×2¾ inch deep pans containing Ray silt loam soil. Selected weed species were planted in separate pans, one-half inch deep soil cover layers (450 gm) were placed on each preseeded pan. Alachlor was then applied to the soil surface with a belt sprayer (20 gpa). The pans were given ¼ inch of overhead water, transferred to greenhouse benches and subirrigated as required for the duration of the test.

The results summarized in Table V are the combined results from two separate tests run at different times but according to the procedure described in Example 19. The seed treatment concentration is calculated based on a %W/W bases, i.e., 1 part of safener per 1000 parts of see, e.g., 1 gram of safener per 1 kilogram of seed.

TABLE V

| Safening Agent Compound of Example No. | Rate of Alachlor Herb. (lb/acre) | % Sorghum Inhibition Seed Treatment Con. % w/w | | | | Rate of Herb. (lb/acre) | % Weed Inhibition | | | | | |
|---|---|---|---|---|---|---|---|---|---|---|---|---|
| | | 0 | .016 | .125 | 1.0 | | SW | LQ | GF | CG | P | BYG |
| 6 | 0 | 0 | 0 | 0 | 0 | 0 | 0 | 0 | 0 | 0 | 0 | 0 |
| | ¼ | 80 | 73 | 63 | 0 — | 1/16 | 80 | 30 | 85 | 93 | 99 | 100 |
| | 1 | 90 | 85 | 83 | 30 — | ¼ | 90 | 55 | 99 | 99 | 99 | 100 |
| | 4 | 100 | 100 | 98 | 63 — | 1 | 97 | 100 | 99 | 99 | 99 | 100 |
| | | | | | | 4 | 100 | 100 | 99 | 100 | 100 | 100 |
| 7 | 0 | 0 | 0 | 0 | 0 | | | | | | | |
| | ¼ | 75 | 75 | 0 — | 0 — | | | | | | | |
| | 1 | 94 | 85 | 40 — | 10 — | | | | | | | |
| | 4 | 100 | 99 | 63 — | 18 — | | | | | | | |
| | | Seed Treatment Con. % w/w | | | | | | | | | | |
| | | 0 | .062 | .250 | 1.0 | | | | | | | |
| 15 | 0 | 0 | 0 | 0 | 0 | 0 | 0 | 0 | 0 | 0 | 0 | 0 |
| | ¼ | 90 | 10 — | 0 — | 0 — | 1/16 | 15 | 25 | 98 | 99 | 98 | 98 |
| | 1 | 98 | 75 — | 28 — | 5 — | ¼ | 45 | 75 | 99 | 99 | 99 | 99 |
| | 4 | 98 | 97 | 73 — | 60 — | 1 | 75 | 90 | 100 | 100 | 100 | 100 |
| | | | | | | 4 | 78 | 100 | 100 | 100 | 100 | 100 |
| 16 | 0 | 0 | 0 | 0 | 30 | | | | | | | |
| | ¼ | 90 | 78 | 30 — | 55 — | | | | | | | |
| | 1 | 97 | 90 | 73 — | 80 | | | | | | | |
| | 4 | 100 | 99 | 98 | 93 | | | | | | | |

— Denotes Significant Safening Effect
SW = Smartweed
LQ = Lamsquarters
GF = Green Foxtail
CG = Crabgrass
P = Panicum
BYG = Barnyard Grass The above examples illustrate that the thiazolecarboxylates of the present invention are useful in reducing herbicidal injury to sorghum plants. The safening agents may be applied to the plant locus as a mixture, i.e., a mixture of a herbicidally effective amount of herbicide and a safening effective amount of safening agent, or sequentially, i.e., the plant locus may be treated with an effective amount of the herbicide followed by a treatment with the safening agent may vary depending upon the crop to be protected, weeds to be inhibited, herbicide used, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, small amounts of safening agent are required to treat such seeds. Table V illustrates that a weight ratio of as little as 0.016 parts of safener per 1000 parts of seed may be effective. The amount of safener utilized in treating the seed may be increased if desired. Generally, however, a weight ratio of safening agent to seed weight may range from 0.125 to 10.0 parts of safening agent per 1000 parts of seed, preferably from about 1.0 to about 10.0 parts of safening agent per 1000 parts of seed. The determination of the effective amount of safening agent required is well within the skill of the art.

Since only a very small amount of active safening agent is usually required for the seed treatment, the compound preferably is formulated as a powder or an emulsifiable concentrate which can be diluted with water by the seed treater for use in the seed treating apparatus. Of course, under certain accommodations, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8-18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkalicasein compositions, long chain alcohols usually containing 10-18 carbon atoms, and condensation products of ethylene oxide with fatty acids, alkylphenols and mercaptans.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of reducing herbicidal injury to sorghum plants due to application thereto of acetanilide herbicides which comprises applying to the plant locus a non-phytotoxic safening effective amount of a compound having the formula

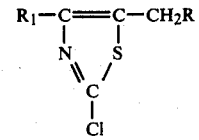

where R is equal to halogen, hydroxy, lower alkoxy or benzyloxy $R_1$ is lower alkyl, halo (lower) alkyl, phenyl, or phenyl substituted by one to three groups, which may be the same or different, selected from the group consisting of halogen, lower alkyl, trifluoromethyl and cyano.

2. A method according to claim 1, wherein $R_1$ is trifluoromethyl.

3. A method according to claim 2 wherein R is halogen, hydroxy or lower alkoxy.

4. A method according to claim 1 wherein $R_1$ is phenyl or phenyl substituted by one or two halogen or trifluoromethyl groups.

5. A method according to claim 4 wherein $R_1$ is phenyl substituted by one or two chloro or fluoro groups.

6. A method according to claim 1 wherein R is halogen, hydroxy or lower alkoxy.

7. A method according to claim 6 wherein $R_1$ is methyl, isopropyl, tert-butyl, trifluoromethyl, p-chlorophenyl or p-fluorophenyl.

8. A method according to claim 1 wherein said herbicide is alachlor, propachlor or butachlor.

9. A method according to claim 8 wherein said herbicide is alachlor.

10. A method according to claim 8 wherein said herbicide is butachlor.

11. A mixture which comprises a herbicidally effective amount of an acetanilide herbicide and a safening effective amount of a compound having the formula

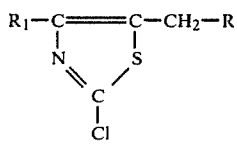

where R is equal to halogen, hydroxy, lower alkoxy, or benzyloxy; $R_1$ is lower alkyl, halo (lower) alkyl, phenyl, or phenyl substituted by one to three groups, which may be the same or different, selected from the group consisting of halogen, lower alkyl, trifluoromethyl and cyano.

12. A mixture according to claim 11 wherein $R_1$ is trifluoromethyl.

13. A mixture according to claim 12 wherein R is halogen, hydroxy or lower alkoxy.

14. A mixture according to claim 11 wherein $R_1$ is phenyl or phenyl substituted by one or two halogen or trifluoromethyl groups.

15. A mixture according to claim 14 wherein $R_1$ is phenyl substituted by one or two chloro or fluoro groups.

16. A mixture according to claim 11 wherein R is halogen, hydroxy, or lower alkoxy.

17. A mixture according to claim 16 wherein $R_1$ is methyl, isopropyl, tert-butyl, trifluoromethyl, p-chlorophenyl or p-fluorophenyl.

18. A mixture according to claim 11 wherein said herbicide is alachlor, propachlor or butachlor.

19. A mixture according to claim 18 wherein said herbicide is alachlor.

20. A mixture according to claim 18 wherein said herbicide is butachlor.

21. A mixture according to claim 11 wherein the ratio of herbicide to safening agent is from about 1:25 parts by weight to about 25:1 parts by weight.

* * * * *